US010420698B2

(12) United States Patent
Jones, Jr. et al.

(10) Patent No.: US 10,420,698 B2
(45) Date of Patent: Sep. 24, 2019

(54) HEAD MASSAGING CAP DEVICE

(71) Applicants: William Jones, Jr., Rancho Palos Verdes, CA (US); Lisa Simmons-Jones, Rancho Palos Verdes, CA (US)

(72) Inventors: William Jones, Jr., Rancho Palos Verdes, CA (US); Lisa Simmons-Jones, Rancho Palos Verdes, CA (US)

( * ) Notice: Subject to any disclaimer, the term of this patent is extended or adjusted under 35 U.S.C. 154(b) by 985 days.

(21) Appl. No.: 14/940,936

(22) Filed: Nov. 13, 2015

(65) Prior Publication Data

US 2017/0135894 A1 May 18, 2017

(51) Int. Cl.

| | |
|---|---|
| ***A61H 7/00*** | (2006.01) |
| ***A61F 7/00*** | (2006.01) |
| *A61H 15/00* | (2006.01) |
| *A61H 23/02* | (2006.01) |

(52) U.S. Cl.

CPC ............. *A61H 7/006* (2013.01); *A61H 7/007* (2013.01); *A61H 15/0078* (2013.01); *A61H 23/02* (2013.01); *A61H 2015/0042* (2013.01); *A61H 2015/0064* (2013.01); *A61H 2201/0207* (2013.01); *A61H 2201/0214* (2013.01); *A61H 2201/0228* (2013.01); *A61H 2201/102* (2013.01); *A61H 2201/105* (2013.01); *A61H 2201/123* (2013.01); *A61H 2201/1654* (2013.01); *A61H 2201/1666* (2013.01); *A61H 2201/50* (2013.01); *A61H 2201/5033* (2013.01); *A61H 2201/5048* (2013.01); *A61H 2205/021* (2013.01)

(58) Field of Classification Search

CPC .... A61H 2201/0207; A61H 2201/0214; A61H 2205/021; A61H 7/006; A61H 15/02; A61H 23/00; A61F 2007/0002; A61F 2007/0008; A61F 2007/0054; A42B 3/285

See application file for complete search history.

(56) References Cited

U.S. PATENT DOCUMENTS 849,844 A * 4/1907 Laurence ............... A61H 7/006 601/136
2,467,007 A * 4/1949 Boyd ..................... A61H 7/006 123/195 A
3,323,517 A * 6/1967 Keller ................ A61H 23/0218 601/18
3,463,161 A * 8/1969 Andrassy .................. A61F 7/02 126/400
3,481,326 A * 12/1969 Schamblin ............. A61H 7/006 601/16

(Continued)

*Primary Examiner* — Rachel T Sippel
*Assistant Examiner* — Christopher E Miller

(57) ABSTRACT

A head massaging cap device for massaging the head includes a shell that is cap shaped. The shell has an inner layer and an outer layer. A compartment is coupled to a front of the shell. A power module is coupled to and positioned in the compartment. A solid state music player is coupled to and positioned in the compartment. A plurality of cooling zones and plurality of heating zones are positioned in the outer layer. A plurality of tracks is positioned on and coupled to an interior surface of the inner layer. The tracks comprise rack gears. Each of a plurality of massage probes is coupled to a respective one of the tracks.

14 Claims, 3 Drawing Sheets

(56) References Cited

U.S. PATENT DOCUMENTS

| | | | | | |
|---|---|---|---|---|---|
| 3,630,039 | A * | 12/1971 | Hayashi | F25B 9/04 | 62/259.3 |
| 3,716,048 | A * | 2/1973 | Alonso | A61H 7/006 | 601/95 |
| 3,763,853 | A * | 10/1973 | Jochimski | A61H 7/006 | 601/70 |
| 4,138,743 | A * | 2/1979 | Elkins | A42B 3/285 | 2/171.2 |
| 4,172,495 | A * | 10/1979 | Zebuhr | A42B 3/285 | 165/46 |
| 4,781,193 | A * | 11/1988 | Pagden | A61F 7/007 | 607/104 |
| 4,869,250 | A * | 9/1989 | Bitterly | A41D 13/0053 | 607/107 |
| 4,998,415 | A * | 3/1991 | Larsen | A41D 13/0053 | 62/231 |
| 5,245,989 | A * | 9/1993 | Simon | A61H 7/006 | 601/108 |
| 5,486,156 | A * | 1/1996 | Takach | A61H 23/0263 | 601/46 |
| 5,557,807 | A * | 9/1996 | Hujar | A42B 1/008 | 2/171.2 |
| 5,603,728 | A * | 2/1997 | Pachys | A61F 7/02 | 607/104 |
| 5,643,336 | A * | 7/1997 | Lopez-Claros | A61F 7/02 | 126/204 |
| 5,682,690 | A * | 11/1997 | Chang | A43B 7/00 | 36/11.5 |
| 5,715,533 | A * | 2/1998 | Stein | A42C 5/04 | 2/7 |
| 5,792,174 | A | 8/1998 | Ioan | | |
| 6,039,704 | A * | 3/2000 | Domenighini | A61H 9/0078 | 601/148 |
| 6,050,099 | A * | 4/2000 | Lopa | A42B 1/008 | 62/259.3 |
| 6,228,041 | B1 * | 5/2001 | Ameer | A61H 23/02 | 601/46 |
| 6,273,865 | B1 | 8/2001 | Perez | | |
| D525,174 | S | 7/2006 | Minowa et al. | | |
| 7,153,283 | B1 | 12/2006 | Triolo et al. | | |
| 7,582,066 | B2 | 9/2009 | Shimotori | | |
| 7,921,473 | B1 * | 4/2011 | Winters | A42B 3/286 | 2/171.3 |
| 9,532,915 | B1 * | 1/2017 | McKinney | A61H 1/00 | |
| 9,867,405 | B1 * | 1/2018 | McFerrin | A41D 13/0053 | |
| 10,021,926 | B2 * | 7/2018 | Stevenson | A41D 20/005 | |
| 2003/0019476 | A1 * | 1/2003 | Chambers | A41D 13/005 | 123/438 |
| 2003/0149382 | A1 * | 8/2003 | Waller | A61H 7/006 | 601/137 |
| 2007/0088234 | A1 | 4/2007 | Tsseng | | |
| 2007/0179571 | A1 * | 8/2007 | De Taboada | A61N 5/0613 | 607/88 |
| 2007/0256212 | A1 * | 11/2007 | Rabin | A42B 1/008 | 2/171 |
| 2008/0097560 | A1 * | 4/2008 | Radziunas | A61F 7/10 | 607/104 |
| 2009/0032049 | A1 * | 2/2009 | Rabin | A42B 1/24 | 132/270 |
| 2009/0281468 | A1 * | 11/2009 | Xu | A61H 7/006 | 601/128 |
| 2010/0106077 | A1 * | 4/2010 | Rabin | A61N 5/0616 | 604/20 |
| 2010/0113991 | A1 * | 5/2010 | Wu | A61H 7/006 | 601/46 |
| 2011/0015707 | A1 * | 1/2011 | Tucker | A61N 5/0616 | 607/90 |
| 2012/0172774 | A1 * | 7/2012 | Lowe | A61F 7/02 | 602/13 |
| 2014/0073996 | A1 | 3/2014 | Jaguan | | |
| 2014/0121577 | A1 | 5/2014 | Ma et al. | | |
| 2017/0165485 | A1 * | 6/2017 | Sullivan | A61N 1/36021 | |
| 2018/0055721 | A1 * | 3/2018 | Quisenberry | A61F 7/02 | |

* cited by examiner

HEAD MASSAGING CAP DEVICE

BACKGROUND OF THE DISCLOSURE

Field of the Disclosure

The disclosure relates to massaging devices and more particularly pertains to a new massaging device for massaging the head.

SUMMARY OF THE DISCLOSURE

An embodiment of the disclosure meets the needs presented above by generally comprising a shell that is cap shaped. The shell has an inner layer and an outer layer. A compartment is coupled to a front of the shell. A power module is coupled to and positioned in the compartment. A solid state music player is coupled to and positioned in the compartment. A plurality of cooling zones and plurality of heating zones are positioned in the outer layer. A plurality of tracks is positioned on and coupled to an interior surface of the inner layer. The tracks comprise rack gears. Each of a plurality of massage probes is coupled to a respective one of the tracks.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
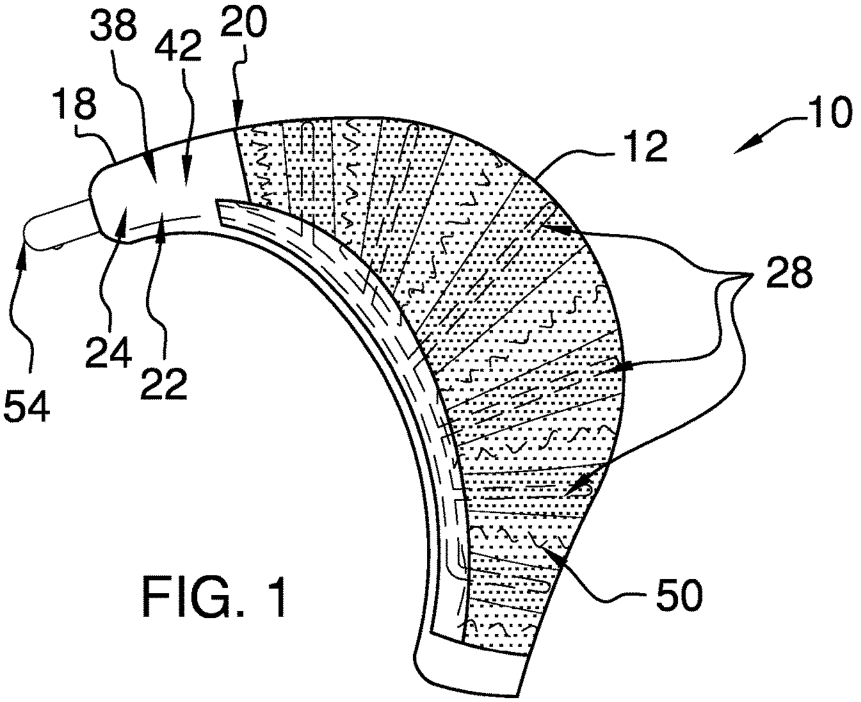
FIG. 1 is a side view of a head massaging cap device according to an embodiment of the disclosure.
Figure 2:
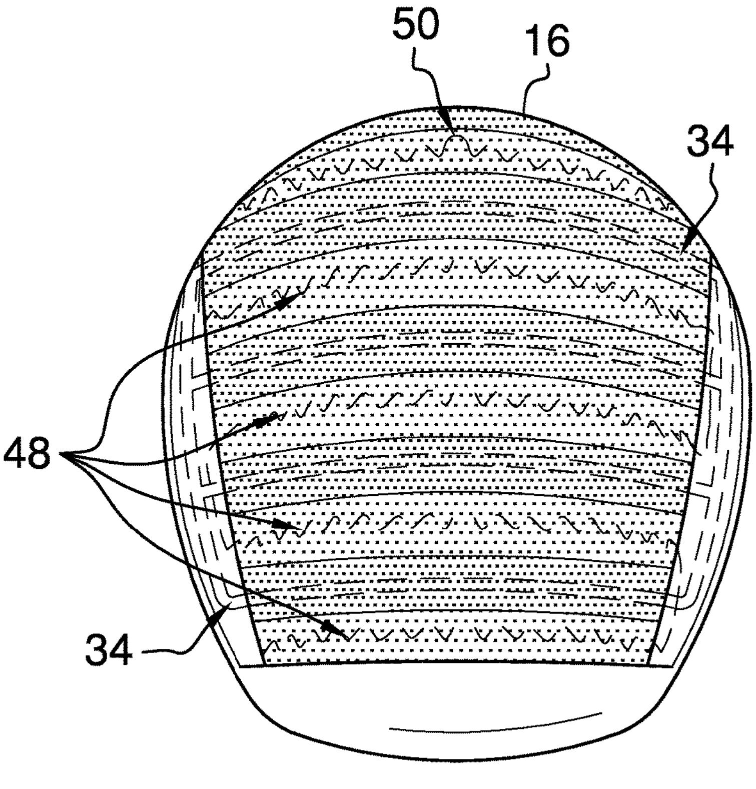
FIG. 2 is a back view of an embodiment of the disclosure.
Figure 3:
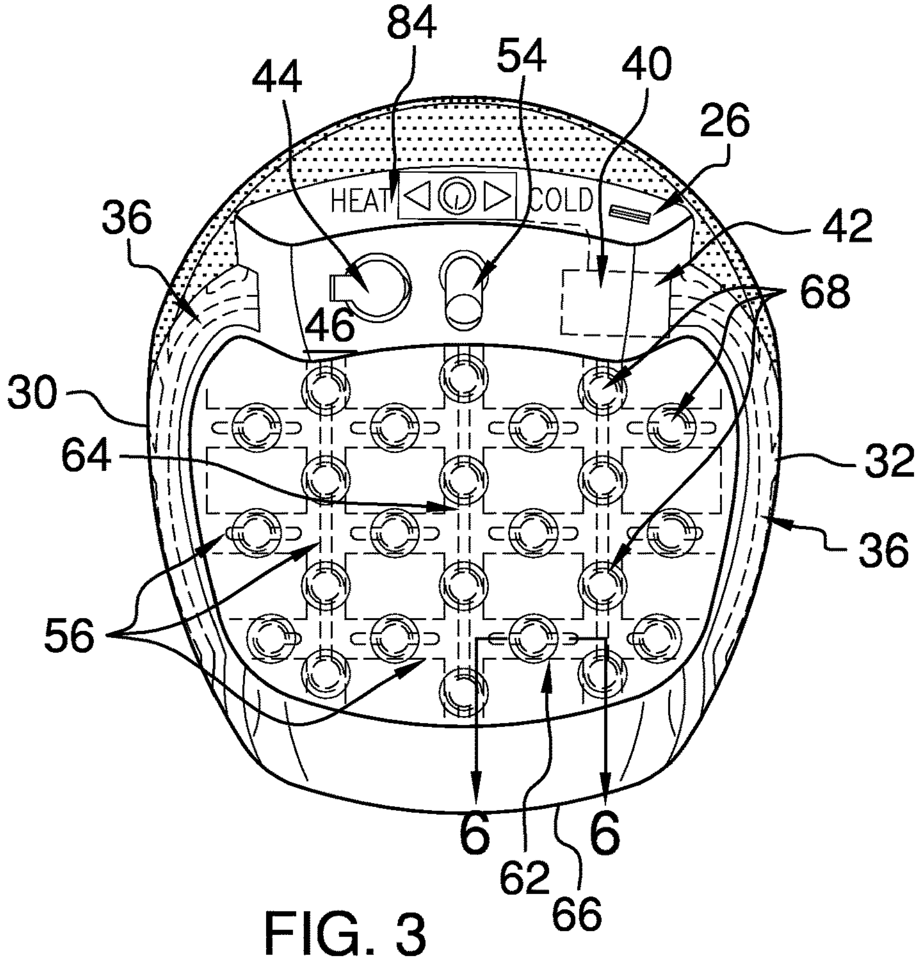
FIG. 3 is a front view of an embodiment of the disclosure.
Figure 4:
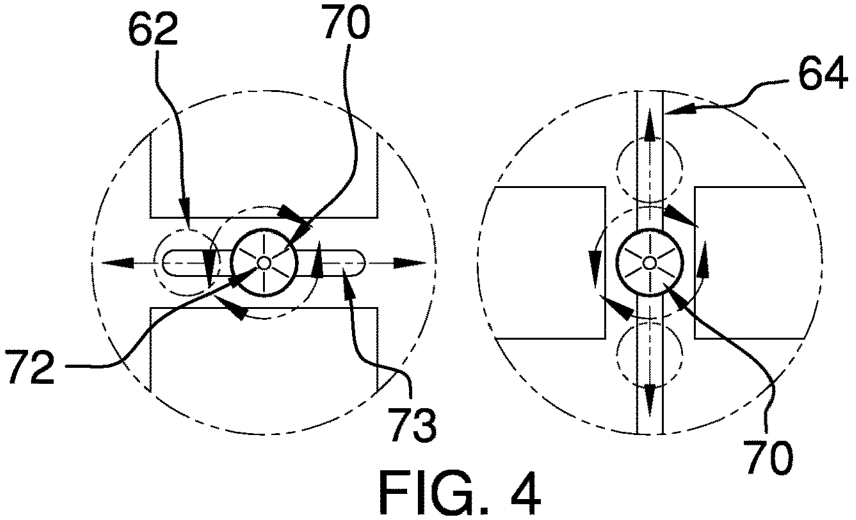
FIG. 4 is a detail view of an embodiment of the disclosure.
Figure 5:
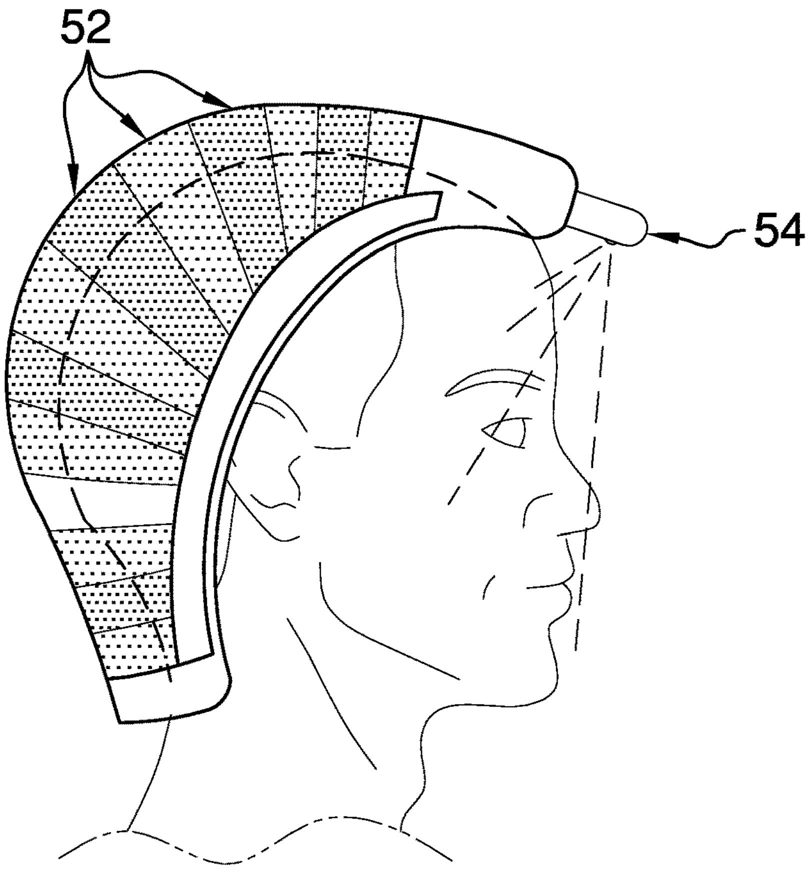
FIG. 5 is an in-use view of an embodiment of the disclosure.
Figure 6:
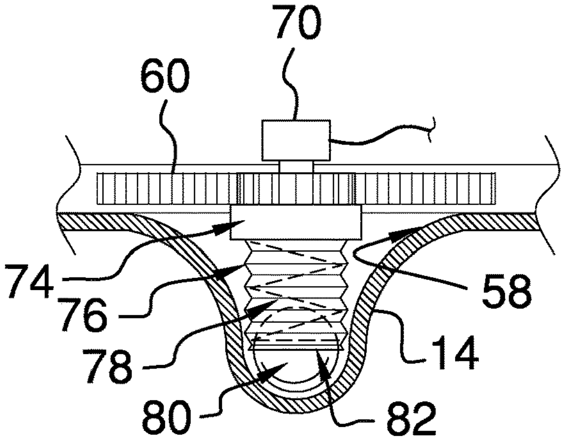
FIG. 6 is a cross-sectional detail view of an embodiment of the disclosure.

With reference now to the drawings, and in particular to FIGS. 1 through 6 thereof, a new massaging device embodying the principles and concepts of an embodiment of the disclosure and generally designated by the reference numeral 10 will be described.

As best illustrated in FIGS. 1 through 6, the head massaging cap device 10 generally comprises a shell 12 that is cap shaped. The shell 12 has an inner layer 14 and an outer layer 16. A compartment 18 is coupled to a front 20 of the shell 12. A power module 22 is coupled to and positioned in the compartment 18. The power module 22 comprises at least one rechargeable battery. A solid state music player 24 is coupled to and positioned in the compartment 18. The player 24 is Bluetooth enabled and is capable of playing MP3 audio files. A female universal serial bus port 26 is positioned in the compartment 18.

A plurality of cooling zones 28 is positioned in the outer layer 16. The cooling zones 28 extend laterally from a left side 30 of the shell 12 to a right side 32 of the shell 12. The cooling zones 28 comprise a tube 34 extending through the cooling zones 28 in a circuit 36. The tube 34 bridges the cooling zones 28 proximate to the left side 30 and the right side 32. A pump 38 is coupled to and positioned in the compartment 18. The pump 38 is operationally coupled to the power module 22 and positioned in the circuit 36. A cooling unit 40 is coupled to and positioned in the compartment 18. The cooling unit 40 is coupled to the power module 22. The cooling unit 40 is positioned in the circuit 36. A reservoir 42 is coupled to and positioned in the compartment 18. The reservoir 42 is positioned in the circuit 36. A plug 44 is positioned in a wall 46 of the compartment 18 proximate to the reservoir 42. The plug 44 is hingedly coupled to the wall 46.

A plurality of heating zones 48 is positioned in the outer layer 16. The heating zones 48 extend laterally from the left side 30 of the shell 12 to the right side 32 of the shell 12. The heating zones 48 comprise a heating element 50 extending through the heating zones 48. The heating element 50 is operationally coupled to the power module 22. The heating element 50 bridges the heating zones 48 proximate to the left side 30 and the right side 32. The cooling zones 28 and the heating zones 48 are positioned in an alternating pattern 52. Preferably, the plurality of cooling zones 28 comprises six cooling zones and the plurality of heating zones 48 comprises seven zones.

A nozzle 54 is coupled to and extends from the compartment 18. The nozzle 54 is operationally coupled to the pump 38.

A plurality of tracks 56 is positioned on and coupled to an interior surface 58 of the inner layer 14. The tracks 56 comprise rack gears 60. The tracks 56 comprise lateral tracks 62 and vertical tracks 64. The lateral tracks 62 extend from proximate to the left side 30 to proximate to the right side 32. The vertical tracks 64 extend from proximate to the front 20 to proximate to a back 66 of the shell 12. The tracks 56 are intersecting.

Each of a plurality of massage the probes 68 is coupled to a respective one of the tracks 56. Each of the probes 68 comprises a motor 70 that is operationally coupled to the power module 22 and a respective one of the plurality of tracks 56. The motor 70 has a shaft 72 that extends through a respective slit 73 in the respective one of the plurality of tracks 56. The motor 70 is capable of imparting rotational and oscillating forces to the shaft 72. The shaft 72 is both extendable and retractable relative to the motor 70. The motor 70 is gearedly coupled to the respective one of the plurality of tracks 56. A guide 74 is positioned below the respective one of the plurality of tracks 56 relative to the motor 70. The guide 74 is fixedly coupled to the shaft 72. A casing 76, which is flexible, is coupled to the guide 74. A spring 78 is positioned in the casing 76 and coupled to the guide 74. A ball 80 is rotationally coupled to a bottom end 82 of the spring 78 and positioned against the inner layer 14.

A control panel 84 is positioned in the compartment 18. The control panel 84 is operationally coupled to the power module 22, the pump 38, the cooling unit 40, the heating element 50, the solid state music player 24 and the plurality of massage probes 68.

In use, the motor 70 is positioned to engage the respective one of the plurality of tracks 56 to move the probe 68 back and forth within the respective slit 73, such that the probe is moveable bi-directionally along the respective slit 73. The motor 70 is coupled to the shaft 72 allowing rotational and oscillating motion to be transferred to the ball 80, as well as massaging movements via extension and retraction of the shaft 72. The device 10 can be placed on the head of the user with the control panel 84 accessible for entering a desired regimen of massage provided by the plurality of massage probes 68. The plug 44 is positioned to allow the user to add water and aromatic compounds to the reservoir 42. The fluid in the circuit 36 is pumped through the cooling unit 40 and then though the tube 34, such that the water and aromatic compounds added by the user to the reservoir 42 can be expelled from the nozzle 54 in a mist, providing aroma therapy. Heating or cooling is provided by the plurality of heating zones 48 or the plurality of cooling zones 28, respectively. The port 26 is positioned for access by the user to recharge the power module 22 and interface with the player 24.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A head massaging cap device comprising:

a shell, said shell being cap shaped, said shell having an inner layer and an outer layer;

a compartment, said compartment being coupled to a front of said shell;

a power module, said power module being coupled to and positioned in said compartment;

a solid state music player, said player being coupled to and positioned in said compartment;

a plurality of cooling zones, said cooling zones being positioned in said outer layer;

a plurality of heating zones, said heating zones being positioned in said outer layer;

a plurality of tracks, said tracks being positioned on and coupled to an interior surface of said inner layer, said tracks comprising rack gears; and a plurality of massage probes, each of said probes being coupled to a respective one of said tracks; each of said probes comprising: a motor, said motor being operationally coupled to said power module and a respective one of said plurality of tracks, said motor having a shaft, said shaft extending through a respective slit in said respective one of said plurality of tracks, said motor being capable of imparting rotational and oscillating forces to said shaft, said shaft being both extendable and retractable relative to said motor, said motor being gearedly coupled to said respective one of said plurality of tracks such that said probe is moveable bi-directionally along said respective slit; a spring, said spring being positioned inside a casing and coupled to a guide, wherein said shaft can be extended to increase the tension of said spring or retracted to reduce the tension on said spring; a ball, said ball being rotationally coupled to a bottom end of said spring and positioned against said inner layer; and wherein said motor is positioned to engage said respective one of said plurality of tracks to move said probe back and forth within said respective slit, said motor being coupled to said shaft allowing rotational and oscillating motion to be transferred to said ball, as well as massaging movements via extension and retraction of said shaft.

2. The device of claim 1, further including a female universal serial bus port, said port being positioned in said compartment, such that said port is positioned for access by the user for recharging said power module and interfacing with said player.

3. The device of claim 1, further including a control panel, said control panel being positioned in said compartment, said control panel being operationally coupled to said power module, a pump, a cooling unit, a heating element, said solid state music player and said plurality of massage probes.

4. The device of claim 1, further comprising:

said cooling zones extending laterally from a left side of said shell to a right side of said shell, said cooling zones comprising a tube extending through said cooling zones in a circuit, said tube bridging said cooling zones proximate to said left side and said right side; and said heating zones extending laterally from a left side of said shell to a right side of said shell, said heating zones comprising a heating element extending through said heating zones, said heating element being operationally coupled to said power module, said heating element bridging said heating zones proximate to said left side and said right side.

5. The device of claim 4, further including said cooling zones and said heating zones being positioned in an alternating pattern.

6. The device of claim 5, further including said plurality of cooling zones comprising six cooling zones, said plurality of heating zones comprising seven zones.

7. The device of claim 1, further comprising:

a pump, said pump being coupled to and positioned in said compartment, said pump being operationally coupled to said power module and positioned in said circuit;

a cooling unit, said cooling unit being coupled to and positioned in said compartment, said cooling unit being coupled to said power module, said cooling unit being positioned in said circuit, wherein fluid in said circuit is pumped through said cooling unit and then though said tube;

a reservoir, said reservoir being coupled to and positioned in said compartment, said reservoir being positioned in said circuit;

a plug, said plug being positioned in a wall of said compartment proximate to said reservoir, said plug being hingedly coupled to said wall, wherein said plug is positioned to allow the user to add water and aromatic compounds to said reservoir.

8. The device of claim 1, further including a nozzle, said nozzle being coupled to and extending from said compartment, said nozzle being operationally coupled to said pump, such that the water and aromatic compounds added by the user to said reservoir can be expelled from said nozzle in a mist.

9. The device of claim 1, further including said tracks comprising lateral tracks and vertical tracks, said lateral tracks extending from proximate to said left side to proximate to said right side, said vertical tracks extending from proximate to said front to proximate to a back of said shell, at least one of said tracks being intersecting.

10. The device of claim 1, further including wherein said guide being positioned below said respective one of said plurality of tracks relative to said motor, said guide being fixedly coupled to said shaft; and said casing being flexible, said casing being coupled to said guide.

11. The device of claim 1, further including said power module comprising at least one rechargeable battery.

12. The device of claim 1, further including said player being Bluetooth enabled.

13. The device of claim 1, further including said player being capable of playing MP3 audio files.

14. A head massaging cap device comprising:

a shell, said shell being cap shaped, said shell having an inner layer and an outer layer;

a compartment, said compartment being coupled to a front of said shell;

a power module, said power module being coupled to and positioned in said compartment, said power module comprising at least one rechargeable battery;

a solid state music player, said player being coupled to and positioned in said compartment, said player being Bluetooth enabled, said player being capable of playing MP3 audio files;

a female universal serial bus port, said port being positioned in said compartment, such that said port is positioned for access by the user for recharging said power module and interfacing with said player;

a plurality of cooling zones, said cooling zones being positioned in said outer layer, said cooling zones extending laterally from a left side of said shell to a right side of said shell, said cooling zones comprising a tube extending through said cooling zones in a circuit, said tube bridging said cooling zones proximate to said left side and said right side;

a pump, said pump being coupled to and positioned in said compartment, said pump being operationally coupled to said power module and positioned in said circuit;

a cooling unit, said cooling unit being coupled to and positioned in said compartment, said cooling unit being coupled to said power module, said cooling unit being positioned in said circuit, wherein fluid in said circuit is pumped through said cooling unit and then though said tube;

a reservoir, said reservoir being coupled to and positioned in said compartment, said reservoir being positioned in said circuit;

a plug, said plug being positioned in a wall of said compartment proximate to said reservoir, said plug being hingedly coupled to said wall, wherein said plug is positioned to allow the user to add water and aromatic compounds to said reservoir;

a plurality of heating zones, said heating zones being positioned in said outer layer, said heating zones extending laterally from a left side of said shell to a right side of said shell, said heating zones comprising a heating element extending through said heating zones, said heating element being operationally coupled to said power module, said heating element bridging said heating zones proximate to said left side and said right side;

said cooling zones and said heating zones being positioned in an alternating pattern; said plurality of cooling zones comprising six cooling zones, said plurality of heating zones comprising seven zones;

a nozzle, said nozzle being coupled to and extending from said compartment, said nozzle being operationally coupled to said pump, such that the water and aromatic compounds added by the user to said reservoir can be expelled from said nozzle in a mist;

a plurality of tracks, said tracks being positioned on and coupled to an interior surface of said inner layer, said tracks comprising rack gears, said tracks comprising lateral tracks and vertical tracks, said lateral tracks extending from proximate to said left side to proximate to said right side, said vertical tracks extending from proximate to said front to proximate to a back of said shell, at least one of said tracks being intersecting;

a plurality of massage probes, each of said probes being coupled to a respective one of said tracks, each of said probes comprising:

a motor, said motor being operationally coupled to said power module and a respective one of said plurality of tracks, said motor having a shaft, said shaft extending through a respective slit in said respective one of said plurality of tracks, said motor being capable of imparting rotational and oscillating forces to said shaft, said shaft being both extendable and retractable relative to said motor, said motor being gearedly coupled to said respective one of said plurality of tracks such that said probe is moveable bi-directionally along said respective slit, a guide, said guide being positioned below said respective one of said plurality of tracks relative to said motor, said guide being fixedly coupled to said shaft, a casing, said casing being flexible, said casing being coupled to said guide, a spring, said spring being positioned in said casing and coupled to said guide, wherein said shaft can be extended to increase the tension on said spring or retracted to reduce the tension on said spring, and a ball, said ball being rotationally coupled to a bottom end of said spring and positioned against said inner layer, wherein said motor is positioned to engage said respective one of said plurality of tracks to move said probe back and forth within said respective slit, said motor being coupled to said shaft allowing rotational and oscillating motion to be transferred to said ball, as well as massaging movements via extension and retraction of said shaft;

a control panel, said control panel being positioned in said compartment, said control panel being operationally coupled to said power module, said pump, said cooling unit, said heating element, said solid state music player and said plurality of massage probes; and wherein said device can be placed on the head of the user with said control panel accessible for entering a desired regimen of massage provided by said plurality of massage probes, aroma therapy emitted from said nozzle, heating or cooling provided by said plurality of heating zones or said plurality of cooling zones, respectively, and audio provided by said player.

* * * * *